US00PP15337P2

(12) United States Plant Patent
Kievit

(10) Patent No.: US PP15,337 P2
(45) Date of Patent: Nov. 16, 2004

(54) ***FUCHSIA* PLANT NAMED 'KIEFUWIND'**

(50) Latin Name: *Fuchsia×hybrida*
Varietal Denomination: Kiefuwind

(75) Inventor: Christa Kievit, Venhuizen (NL)

(73) Assignee: Kieft Bloemzaden B.V., Venhuizen (NL)

( * ) Notice: Subject to any disclaimer, the term of this patent is extended or adjusted under 35 U.S.C. 154(b) by 0 days.

(21) Appl. No.: 10/787,052

(22) Filed: Feb. 25, 2004

(51) Int. Cl.[7] ..... A01H 5/00
(52) U.S. Cl. ..... Plt./300
(58) Field of Search ..... Plt./300

(56) References Cited

PUBLICATIONS

UPOV–ROM GTITM, Plant Variety Database, 2004/02, GTI Jouve Retrieval Software, Citation for *Fuchsia* 'Kiefuwind'.*

* cited by examiner

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Fuchsia* plant named 'Kiefuwind', characterized by its compact, upright and outwardly spreading plant habit; freely branching habit; full and dense plant growth habit; dark pink and white-colored flowers; and freely and continuous flowering habit.

1 Drawing Sheet

Botanical classification/cultivar designation: *Fuchsia×hybrida* cultivar Kiefuwind.

BACKGROUND OF THE INVENTION

The present invention relates to a new and distinct cultivar of *Fuchsia* plant, botanically known as *Fuchsia×hybrida*, and hereinafter referred to by the name 'Kiefuwind'.

The new *Fuchsia* is a product of a planned breeding program conducted by the Inventor in Venhuizen, The Netherlands. The objective of the breeding program was to create new *Fuchsia* cultivars with compact plant habit and numerous attractive flower coloration.

The new *Fuchsia* originated from a cross-pollination made by the Inventor during the late winter of 1998 of a proprietary selection *Fuchsia×hybrida* identified as code number 6265-3, not patented, as the female, or seed, parent with a proprietary selection *Fuchsia×hybrida* identified as code number 265, not patented, as the male, or pollen, parent. The cultivar Kiefuwind was discovered and selected by the Inventor as a flowering plant within the progeny of the stated cross-pollination in a controlled environment in Venhuizen, The Netherlands.

Asexual reproduction of the new *Fuchsia* by terminal cuttings at Venhuizen, The Netherlands, since the summer of 1998 has shown that the unique features of this new *Fuchsia* are stable and reproduced true to type in successive generations.

BRIEF SUMMARY OF THE INVENTION

The cultivar Kiefuwind has not been observed under all possible environmental conditions. The phenotype may vary somewhat with variations in environment such as temperature and daylength, without, however, any variance in genotype.

The following traits have been repeatedly observed and are determined to be the unique characteristics of 'Kiefuwind'. These characteristics in combination distinguish 'Kiefuwind' as a new and distinct *Fuchsia* cultivar:

1. Compact, upright and outwardly spreading plant habit.
2. Freely branching habit; dense and full plant growth habit.
3. Dark pink and white-colored flowers.
4. Freely and continuous flowering habit.

Plants of the new *Fuchsia* differ from the female parent selection primarily in flower coloration. Compared to plants of the male parent selection, plants of the new *Fuchsia* are more outwardly spreading and differ in flower coloration.

Plants of the new *Fuchsia* can be compared to plants of the cultivar Tom Thumb, not patented. In side-by-side comparisons conducted in Venhuizen, The Netherlands, plants of the new *Fuchsia* differed from plants of the cultivar Tom Thumb in the following characteristics:

1. Plants of the new *Fuchsia* were more upright and outwardly spreading than plants of the cultivar Tom Thumb.
2. Flowers of plants of the new *Fuchsia* were positioned above and beyond the foliage whereas flowers of plants of the cultivar Tom Thumb were positioned within the foliage.
3. Plants of the new *Fuchsia* had better garden performance than plants of the cultivar Tom Thumb.

BRIEF DESCRIPTION OF THE PHOTOGRAPHS

The accompanying colored photographs illustrate the overall appearance of the new *Fuchsia*, showing the colors as true as it is reasonably possible to obtain in colored reproductions of this type. Colors in the photographs may differ slightly from the color values cited in the detailed botanical description which accurately describe the colors of the new *Fuchsia*.

The photograph at the top of the sheet comprises a side perspective view of a typical potted plant of 'Kiefuwind'.

The photograph at the bottom sheet is a close-up view of developing flower buds, fully opened flowers, and upper and lower surfaces of typical leaves of 'Kiefuwind'.

DETAILED BOTANICAL DESCRIPTION

The aforementioned photographs and following observations and measurements describe plants grown in Lompoc, Calif., under commercial practice during the winter and early spring in a polycarbonate-covered greenhouse with day temperatures about 18 to 24° C., night temperatures about 16 to 18° C., and light levels about 4,000 to 8,000 foot-candles. One cutting was planted per 15-cm container and plants were grown for about 13 weeks. In the following description, color references are made to The Royal Horticultural Society Colour Chart, 1995 Edition, except where general terms of ordinary dictionary significance are used.

Botanical classification: *Fuchsia×hybrida* cultivar Kiefuwind.

Parentage:

*Female or seed parent.*—Proprietary selection of *Fuchsia×hybrida* identified as code number 6265-3, not patented.

*Male, or pollen, parent.*—Proprietary selection of *Fuchsia×hybrida* identified as code number 265, not patented.

Propagation:

*Type cutting.*—Terminal cuttings.

*Time to initiate roots, summer and winter.*—About 14 days at 21° C.

*Time to produce a rooted cutting.*—Summer: About 28 days at 21° C. Winter: About 32 days at 21° C.

*Root description.*—Fine, fibrous and white in color.

*Rooting habit.*—Freely-branching.

Plant description:

*Form.*—Upright, outwardly spreading and pendulous plant habit, relatively compact and freely branching habit; dense and full plants. Freely flowering. Appropriate for 10 to 15-cm containers. Moderately vigorous.

*Plant height at flowering.*—About 15 cm.

*Plant diameter at flowering.*—About 28 cm.

*Branching habit.*—Freely branching; typically 12 lateral branches develop per plant. Pinching (removal of terminal apex) enhances lateral branch development.

*Lateral branch description.*—Length: About 15 cm. Diameter: About 3 mm. Internode length: About 2 cm. Aspect: Initially upright to pendulous with flower development. Strength: Moderately strong. Texture: Slightly pubescent. Color: 183D.

*Foliage description.*—Arrangement: Simple, opposite. Length: About 4 cm. Width: About 2.3 cm. Shape: Elliptic. Apex: Acute. Base: Nearly cordate. Margin: Serrulate. Texture, upper and lower surfaces: Smooth, glabrous. Venation pattern: Pinnate. Petiole length: About 8 mm. Petiole diameter: About 2 mm. Petiole texture, upper and lower surfaces: Smooth, glabrous. Color: Developing leaves, upper surface: 137A. Developing leaves, lower surface: 137D. Fully expanded leaves, upper surface: 147A. Fully expanded leaves, lower surface: 147B. Venation, upper and lower surfaces: 147C. Petiole, upper and lower surfaces: 144B.

Flower description:

*Flower type and habit.*—Single bi-colored axillary flowers. Freely flowering; potentially two flowers per leaf axil; about four open flowers and about four flower buds per lateral branch. Flowers not persistent. Flowers not fragrant.

*Natural flowering season.*—April through October in northern Europe; flowering continuous.

*Flower longevity.*—Flowers last about four to five days on the plant.

*Flower orientation.*—Initially upright, then pendulous.

*Flower diameter.*—About 6.2 cm.

*Flower height.*—About 6 cm.

*Flower buds.*—Shape: Ovoid. Length: About 3.7 cm. Width: About 1.2 cm. Color: 55A.

*Petals.*—Quantity: Four; imbricate. Length: About 2 cm. Width: About 2.2 cm. Shape: Fan-shaped. Apex: Rounded. Margin: Entire. Texture, upper and lower surfaces: Glabrous, smooth and satiny. Color: When opening, upper surface: 155C. When opening, lower surface: 155D. Fully opened, upper and lower surfaces: 155D; towards base, 62A.

*Sepals.*—Quantity: Four; fused at base. Length: About 4.2 cm. Width: About 8 mm. Aspect: Flat; recurved. Shape: Elliptic. Apex: Acute. Margin: Entire. Texture, upper and lower surfaces: Glabrous, smooth. Color: When opening, upper and lower surfaces: 55A. Fully opened, upper and lower surfaces: 55B.

*Peduncles.*—Length: About 3.5 cm. Diameter: About 1.5 mm. Aspect: Arching to horizontal. Strength: Moderately strong. Texture: Smooth, glabrous. Color: 144A.

*Reproductive organs.*—Stamens: Stamen number: Eight per flower. Anther length: About 3 mm. Anther diameter: About 2 mm. Anther shape: Oblong. Anther color: 52A. Filament length: About 6.2 cm. Filament color: Close to 66C. Pollen amount: Moderate. Pollen color: 156D. Pistils: Pistil number: One per flower. Pistil length: About 9.1 cm. Style color: 55B. Stigma shape: Oblong. Stigma color: 2D. Ovary color: 144A.

*Seed/fruit.*—Seed and fruit production has not been observed.

Disease/pest resistance: Plants of the new *Fuchsia* have not been observed to be resistant to pathogens and pests common to *Fuchsias*.

Temperature tolerance: Plants of the new *Fuchsia* have been observed to tolerate low temperatures of 10° C. and high temperatures of 30° C.

Garden performance: Plants of the new *Fuchsia* perform have been observed to perform well in the garden and are tolerant to rain and wind.

It is claimed:

1. A new and distinct cultivar of *Fuchsia* plant named 'Kiefuwind', as illustrated and described.

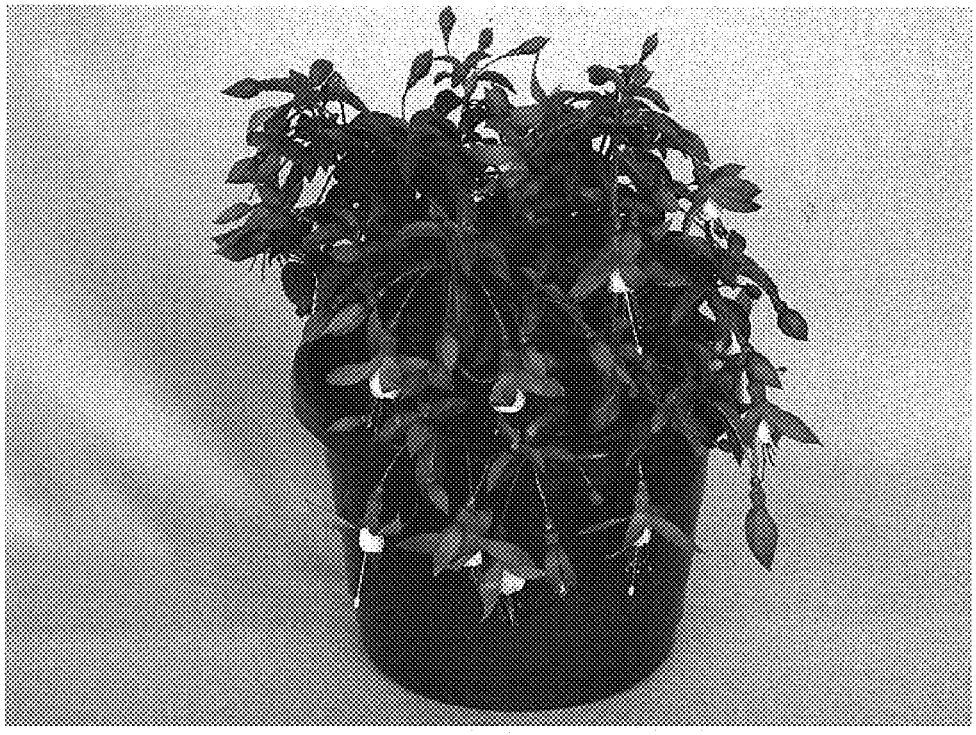
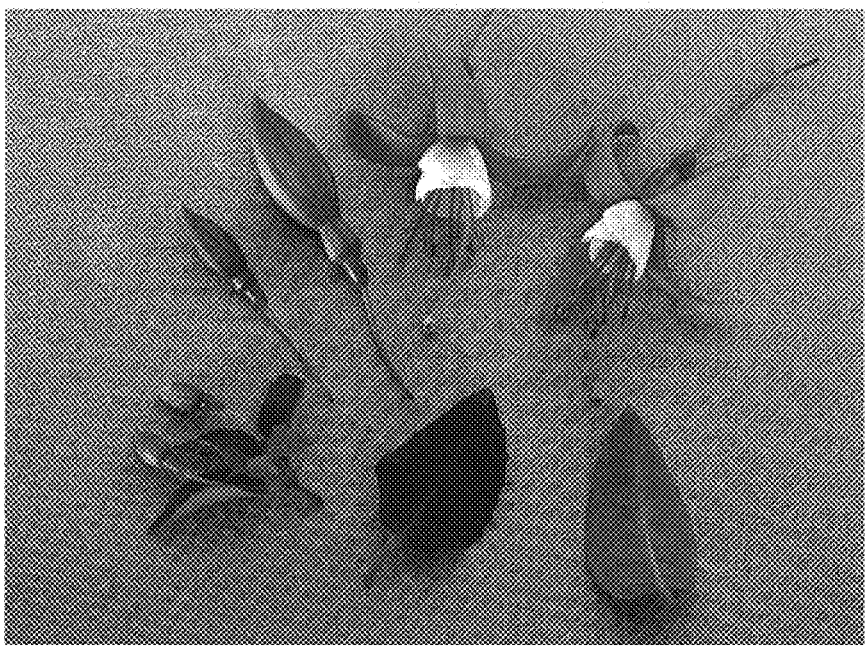

* * * * *